United States Patent
Egami et al.

(10) Patent No.: US 8,307,532 B2
(45) Date of Patent: Nov. 13, 2012

(54) TUBULAR STRUCTURE FOR FIXING PARTICULATE MATTER DETECTION DEVICE

(75) Inventors: Takashi Egami, Tokoname (JP); Takeshi Sakuma, Nagoya (JP); Masahiro Tokuda, Nagoya (JP); Atsuo Kondo, Okazaki (JP)

(73) Assignee: NGK Insulators, Ltd., Nagoya (JP)

( * ) Notice: Subject to any disclaimer, the term of this patent is extended or adjusted under 35 U.S.C. 154(b) by 433 days.

(21) Appl. No.: 12/694,502

(22) Filed: Jan. 27, 2010

(65) Prior Publication Data

US 2010/0229371 A1    Sep. 16, 2010

(30) Foreign Application Priority Data

Mar. 12, 2009  (JP) ................................. 2009-058853

(51) Int. Cl.
*G01R 31/28* (2006.01)
*B23Q 17/00* (2006.01)

(52) U.S. Cl. ......................... 29/593; 29/407.05; 204/424

(58) Field of Classification Search ............... 29/407.05, 29/407.01, 428, 592.1, 593, 729; 204/424, 204/427, 428
See application file for complete search history.

(56) References Cited

U.S. PATENT DOCUMENTS

| | | | |
|---|---|---|---|
| 5,089,133 A | 2/1992 | Kato et al. | |
| 5,800,689 A | 9/1998 | Hori et al. | |
| 2002/0000033 A1 | 1/2002 | Tajima et al. | |
| 2005/0247561 A1* | 11/2005 | Chiu et al. ..................... | 204/424 |
| 2010/0071441 A1 | 3/2010 | Sakuma et al. | |

FOREIGN PATENT DOCUMENTS

| | | |
|---|---|---|
| EP | 0 624 790 | 11/1994 |
| EP | 0 702 229 | 3/1996 |
| GB | 2 309 312 | 7/1997 |
| JP | 60-123761 A1 | 7/1985 |
| JP | 02-238354 A1 | 9/1990 |
| JP | 05-087769 | 4/1993 |
| JP | 2010-078428 A1 | 4/2010 |

\* cited by examiner

*Primary Examiner* — John C Hong
(74) *Attorney, Agent, or Firm* — Burr & Brown (57) ABSTRACT

A tubular structure for fixing a particulate matter detection device including a tubular first holding tube having a fixing structure portion at a first end; and a tubular second holding tube having one end fixed to a second end so that the second holding tube is coaxial with the first holding tube. The particulate matter detection device is prolonged in one direction and having a detecting portion for particulate matter, with a takeout portion of a wiring line disposed in the tubular structure so that the detecting portion projects to the outside from the first end and so that the takeout portion is positioned in the second holding tube, and with the particulate matter detection device fixed to a pipe by the fixing structure portion so that the detecting portion is positioned in the pipe.

20 Claims, 5 Drawing Sheets

TUBULAR STRUCTURE FOR FIXING PARTICULATE MATTER DETECTION DEVICE

BACKGROUND OF THE INVENTION

1. Field of the Invention

The present invention relates to a tubular structure for fixing a particulate matter detection device. More particularly, it relates to a tubular structure for fixing particulate matter detection device which is excellent in heat release properties.

2. Description of the Related Art

A flue exhaust gas or a diesel engine exhaust gas includes particulate matter (PM) such as soot, and has been a cause for air pollution. To remove this particulate matter, a filter (a diesel particulate filter: DPF) made of a ceramic material or the like is broadly used. The ceramic DPF can be used for a long period of time, but a defect such as cracking or melting sometimes occurs owing to heat deterioration or the like, and the particulate matter might leak, though its amount is small. When such a defect occurs, it is remarkably important from the viewpoint of the prevention of the air pollution to immediately detect the occurrence of the defect and to recognize the abnormality of the device. As a method of detecting the occurrence of such a defect, a method is suggested in which a particulate matter (PM) detection device is disposed on the downstream side of the DPF (e.g., see Patent Document 1).

Moreover, it is similarly important to detect nitrogen oxide (NOx) from the viewpoint of the prevention of the air pollution, and a nitrogen oxide detection device is suggested (e.g., see Patent Document 2).

[Patent Document 1] JP-A-60-123761
[Patent Document 2] JP-A-02-238354

The above particulate matter detection device or nitrogen oxide detection device is usually attached to an exhaust gas passing pipe or the like, to detect the particulate matter or nitrogen oxide included in the exhaust gas which circulates through the pipe. However, if this device is attached to, for example, a pipe for discharging the exhaust gas from a car engine, a stone struck up by a moving car or the like might collide with the device to break down the device. To solve the problem, it has also been suggested that, for example, the outside of the detection device be covered with a double tube and fixed to the pipe.

However, when the outside of the particulate matter detection device is covered with the double tube, for example, a problem occurs that the inside of the device has a high temperature, whereby a measured value becomes inaccurate.

The present invention has been developed in view of such problems of the conventional technology, and an object thereof is to provide a tubular structure for fixing particulate matter detection device which is excellent in heat release properties.

SUMMARY OF THE INVENTION

To achieve the above object, according to the present invention, there is provided a tubular structure for fixing a particulate matter detection device as follows.

According to a first aspect of the present invention, the tubular structure for fixing a particulate matter detection device is provided, comprising: a tubular first holding tube having a fixing structure portion at a first end as one end thereof; and a tubular second holding tube having one end fixed to a second end as the other end of the first holding tube so that the second holding tube is coaxial with the first holding tube, wherein the particulate matter detection device made of a ceramic material, prolonged in one direction and having a detecting portion of a particulate matter at one end thereof and a takeout portion of a wiring line at the other end thereof is disposed so that the detecting portion projects to the outside from the first end of the first holding tube and so that the takeout portion of the wiring line is positioned in the second holding tube, and the particulate matter detection device is fixed to a pipe of an exhaust gas by the fixing structure portion of the first holding tube so that the detecting portion of the particulate matter detection device is positioned in the pipe of the exhaust gas.

According to a second aspect of the present invention, the tubular structure for fixing the particulate matter detection device according to the first aspect is provided, wherein the first holding tube has a plurality of linear projections extending in a central axis direction thereof over the whole outer periphery thereof.

According to a third aspect of the present invention, the tubular structure for fixing the particulate matter detection device according to the first or second aspect is provided, wherein the second holding tube has a plurality of linear projections extending in the central axis direction thereof over the whole outer periphery thereof.

According to a fourth aspect of the present invention, the tubular structure for fixing the particulate matter detection device according to the second or third aspect is provided, wherein the linear projections have heights of 0.5 to 5 mm.

According to a fifth aspect of the present invention, the tubular structure for fixing the particulate matter detection device according to any one of the first to fourth aspects is provided, wherein the first holding tube has a length of 40 to 90 mm.

According to a sixth aspect of the present invention, the tubular structure for fixing the particulate matter detection device according to any one of the first to fifth aspects is provided, wherein the fixing structure portion of the first holding tube has a thread structure.

According to a seventh aspect of the present invention, a fixing method of a particulate matter detection device is provided, the method comprising the steps of: disposing, in the tubular structure for fixing the particulate matter detection device according to any one of the first to sixth aspects is provided, the particulate matter detection device made of a ceramic material, prolonged in one direction and having a detecting portion of a particulate matter at one end thereof and a takeout portion of a wiring line at the other end thereof so that the detecting portion projects to the outside from the first end of the first holding tube and so that the takeout portion of the wiring line is positioned in the second holding tube; and fixing the particulate matter detection device to a pipe for an exhaust gas by the fixing structure portion of the first holding tube so that the detecting portion of the particulate matter detection device is positioned in the pipe for the exhaust gas.

According to the tubular structure for fixing the particulate matter detection device of the present invention, in a case where the particulate matter detection device is fixed to the pipe through which the exhaust gas flows and a high temperature exhaust gas circulates through the pipe, the tubular structure for fixing the particulate matter detection device has satisfactory heat release properties, and hence a measured value is prevented from becoming inaccurate or fluctuating. Moreover, according to the fixing method of the particulate matter detection device of the present invention, the particulate matter detection device is fixed to the pipe through which the exhaust gas flows, by use of the tubular structure for fixing the particulate matter detection device of the present invention. Therefore, even when the high temperature exhaust gas circulates through the pipe, the tubular structure for fixing the particulate matter detection device has satisfactory heat release properties, and hence the measured value is prevented from becoming inaccurate or fluctuating.

DETAILED DESCRIPTION OF THE INVENTION

Next, embodiments of the present invention will be described in detail with reference to the drawings, but it should be understood that the present invention is not limited to the following embodiments and that the appropriate alteration, improvement or the like of the design is added based on the ordinary knowledge of a person with ordinary skill without departing from the scope of the present invention.

Figure 1:
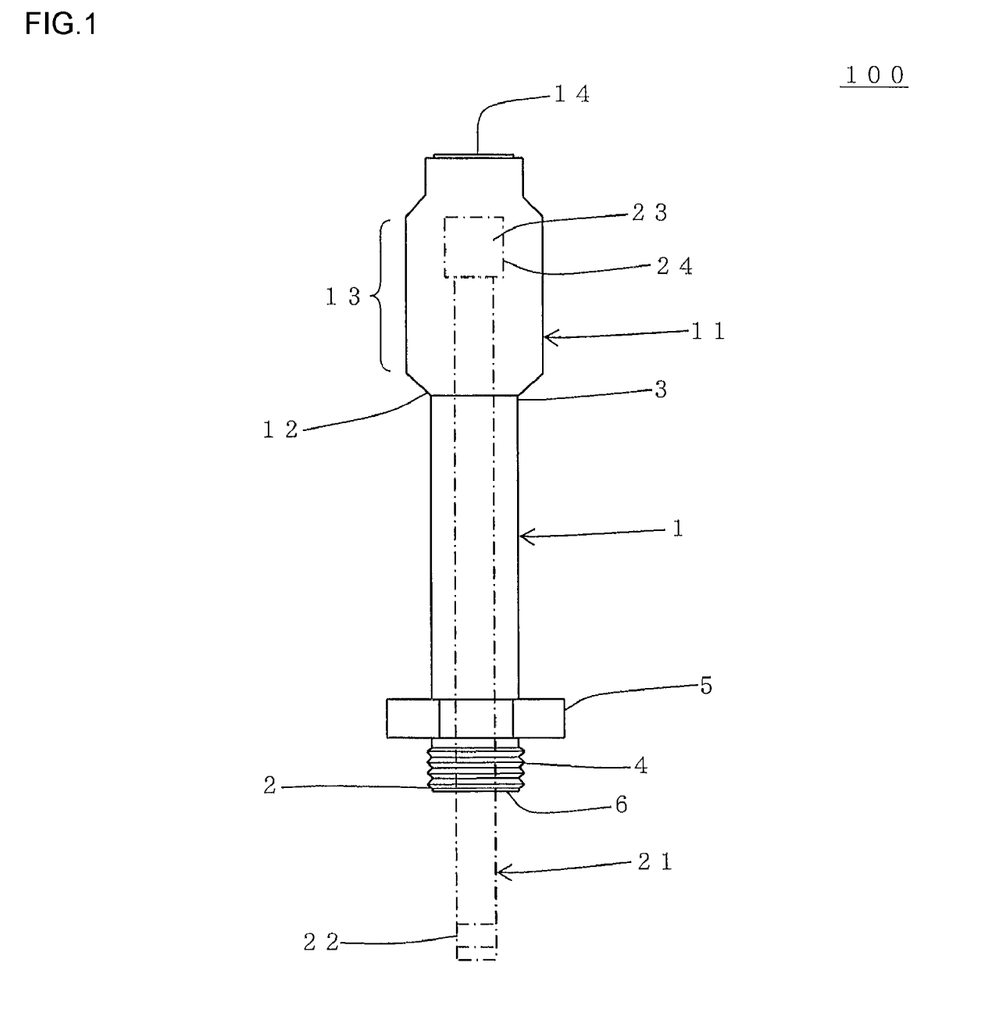
FIG. 1 is a side view schematically showing one embodiment of a tubular structure for fixing a particulate matter detection device of the present invention.
Figure 2:
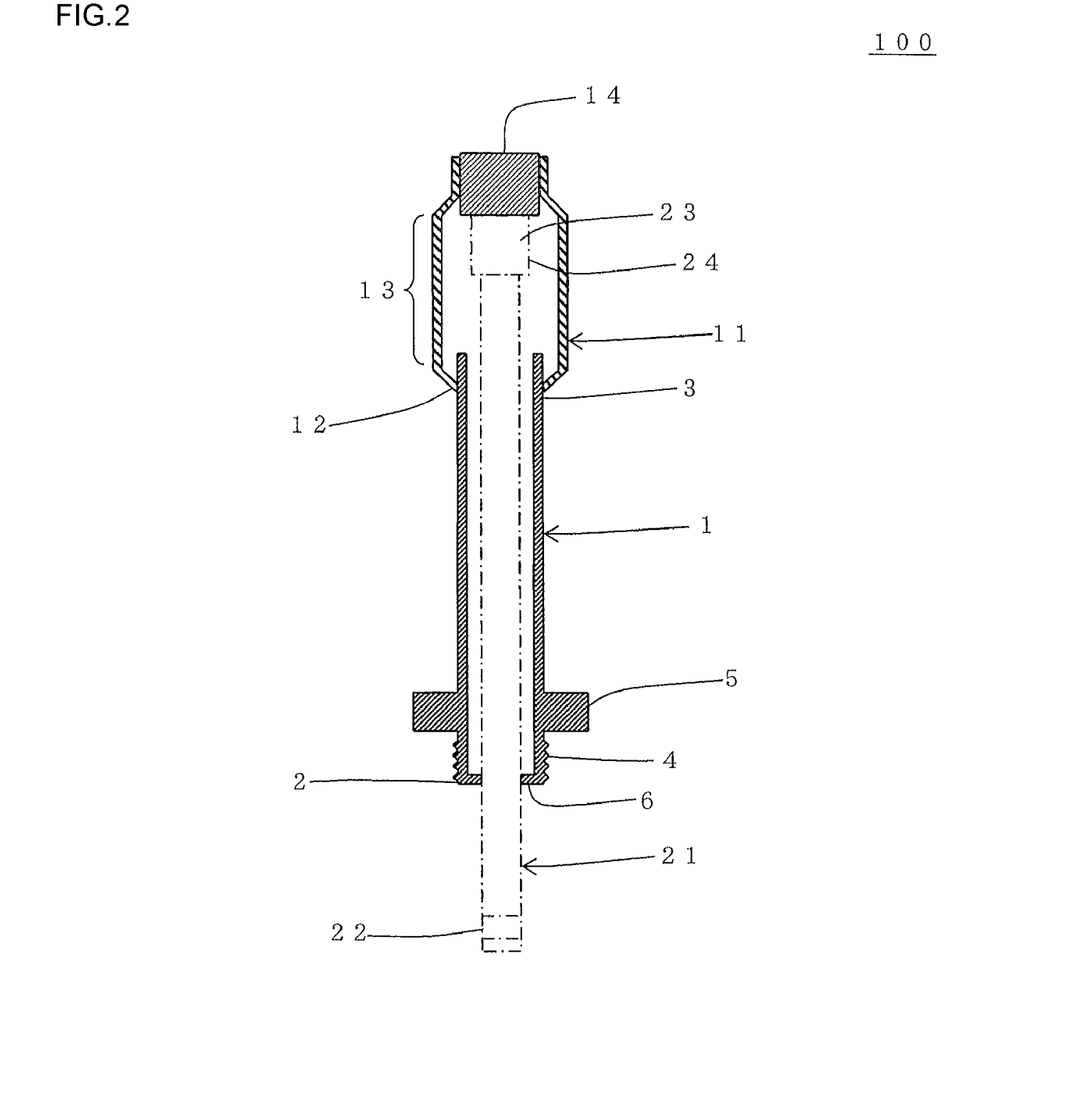
FIG. 2 is a schematic diagram showing a cross section of the embodiment of the tubular structure for fixing the particulate matter detection device of the present invention cut along a plane parallel to a central axis direction.

(1) Tubular Structure for Fixing Particulate Matter Detection Device:

As shown in FIGS. 1 and 2, one embodiment of a tubular structure for fixing a particulate matter detection device of the present invention (hereinafter referred to simply as "the tubular structure") includes a tubular first holding tube 1 having a fixing structure portion 4 at a first end 2 as one end thereof, and a tubular second holding tube 11 having one end 12 fixed to a second end 3 as the other end of the first holding tube 1 so that the second holding tube is coaxial with the first holding tube 1. Moreover, in the tubular structure for fixing particulate matter detection device 100 of the present embodiment, a particulate matter detection device 21 made of a ceramic material, prolonged in one direction and having a detecting portion 22 of particulate matter at one end thereof and a takeout portion 23 of a wiring line at the other end thereof, is disposed so that the detecting portion 22 projects to the outside from the first end 2 of the first holding tube 1 where the takeout portion 23 of the wiring line is positioned in the second holding tube 11, and the particulate matter detection device is fixed to a pipe of an exhaust gas by the fixing structure portion 4 of the first holding tube 1, so that the detecting portion 22 of the particulate matter detection device 21 is positioned in the pipe of the exhaust gas. FIG. 1 is a side view schematically showing the embodiment of the tubular structure for fixing the particulate matter detection device of the present invention. FIG. 2 is a schematic diagram showing a cross section of the embodiment of the tubular structure for fixing the particulate matter detection device of the present invention cut along a plane parallel to a central axis direction.

The first holding tube 1 of the tubular structure 100 of the present embodiment is a cylindrical member having the fixing structure portion 4 at the first end 2 as one end thereof. The first holding tube 1 is a cylindrical single tube, and hence has satisfactory heat release properties, whereby the inside of the tube can be prevented from becoming high in temperature. The first holding tube 1 is preferably cylindrical, but there is not any special restriction on the shape of the tube as long as the tube is a single tube, and the cross section of the tube crossing the central axis at right angles may have a polygonal shape such as a hexagonal shape or an octagonal shape, or an elliptic shape. A distance (a length of an externally exposed portion) of the first holding tube 1 between the tip of the first end 2 and a portion bonded to the second holding tube 11 is preferably from 40 to 70 mm, further preferably 50 to 60 mm. If the distance is shorter than 40 mm and the tubular structure 100 of the present embodiment is fixed to the pipe, a distance between the pipe and the second holding tube 11 shortens, and the takeout portion 23 of the particulate matter detection device 21 disposed in the second holding tube 11 becomes high in temperature. If the distance is longer than 70 mm, the whole tubular structure 100 of the present embodiment lengthens, and is not easily used in a narrow place as in a case where the device is fixed to the pipe of the exhaust gas from the car engine. It is to be noted that in FIGS. 1 and 2, the takeout portion 23 of the particulate matter detection device 21 is hidden in a contact member 24.

The outer diameter of the cross section of the first holding tube 1 crossing the central axis thereof at right angles is preferably from 10 to 20 mm, further preferably from 12 to 16 mm. If the diameter is smaller than 10 mm, the particulate matter detection device does not easily enter the tube, and heat release becomes insufficient. If the diameter is larger than 20 mm, the device cannot easily be used in the narrow place as in a case where the device is fixed to the pipe for the exhaust gas from the car engine. The thickness of a wall of the first holding tube (the wall thickness) is preferably from 0.3 to 1.5 mm, further preferably from 0.5 to 1.0 mm. If the thickness is smaller than 0.3 mm, strength lowers. If the thickness is larger than 1.5 mm, the heat release becomes insufficient.

The tip portion of the first end 2 of the first holding tube 1 has a bottom portion 6 provided with a through hole through which the particulate matter detection device 21 passes. The through hole formed in the bottom portion preferably has such a size that when the particulate matter detection device 21 is passed through the hole, a gap of 0.1 to 0.5 mm is formed between the periphery of the hole and the particulate matter detection device 21. Therefore, the tip portion of the first end 2 of the first holding tube 1 is closed with the bottom portion 6 and the particulate matter detection device 21, which prevents the exhaust gas in the pipe from entering the tip portion of the first end 2 of the first holding tube 1.

In the tubular structure 100 of the present embodiment, the fixing structure portion 4 formed at the first end 2 of the first holding tube 1 has a thread structure. That is, the tubular structure 100 of the present embodiment is provided with an external thread as the fixing structure portion 4 at the first end 2 of the first holding tube 1. Accordingly, the forming of an internal thread on a pipe side enables the fixing of the tubular structure 100 to the pipe by thread fastening. Moreover, the tubular structure 100 of the present embodiment has a flange portion 5 having a hexagonal cross section crossing the central axis at right angles so that the structure is tightened by a spanner, a monkey wrench or the like when thread-fastened to the pipe. Consequently, when the tubular structure 100 is fixed to the pipe by the thread fastening, the flange portion 5 is held and turned by the tip of the spanner, the monkey wrench or the like, thereby enabling the thread fastening.

Moreover, the first holding tube 1 may be constituted by the first end 2 and a trunk portion which is independent of the first end 2 and which is a portion other than the first end 2. Furthermore, at the first end 2, the fixing structure portion 4 and the flange portion 5 may be integrally formed. Additionally, in this case, the integrally formed fixing structure portion 4 and flange portion 5 are preferably attached to the trunk portion independently of the trunk portion so that they can be rotated at the end of the trunk portion. Moreover, the integrally formed fixing structure portion 4 and flange portion 5 preferably have a ring-shaped stopper portion near the first end 2 of the trunk portion of the first holding tube 1 so that they do not move toward the second end of the first holding tube 1.

There is not any special restriction on the material of the first holding tube 1, but, for example, inexpensive stainless steel having a high strength is preferable. As the type of stainless steel, austenite-based steel or the like is preferable.

The second holding tube 11 of the tubular structure 100 of the present embodiment is a cylindrical single tube having one end 12 fixed to a second end 3 as the other end of the first holding tube 1, so that the second holding tube is coaxial with the first holding tube 1. The second holding tube 11 is the cylindrical single tube, and hence has satisfactory heat release properties, whereby the inside of the tube can be prevented from having a high temperature. The second holding tube 11 is preferably cylindrical in this manner, but there is not any special restriction on the shape of the tube as long as the tube is the single tube, and the cross section of the tube crossing the central axis at right angles may have a polygonal shape, such as a hexagonal shape or an octagonal shape, or an elliptic shape. The length of the second holding tube 11 in the central axis direction is preferably from 30 to 60 mm, further preferably 40 to 50 mm. If the length is shorter than 30 mm, the takeout portion 23 of the tubular structure 100 of the present embodiment cannot be received in the tube. If the length is longer than 60 mm, the whole tubular structure 100 of the present embodiment lengthens, and cannot be easily used in the narrow place, as in the case where the detection device is fixed to the pipe of the exhaust gas from the car engine.

The outer diameter of the cross section of the second holding tube 11 crossing the central axis at right angles is preferably from 15 to 25 mm, further preferably from 17 to 20 mm. If the diameter is smaller than 15 mm, the particulate matter detection device does not easily enter the tube, or heat release becomes insufficient. If the diameter is larger than 25 mm, the structure cannot easily be used in the narrow place, as in the case where the device is fixed to the pipe of the exhaust gas from the car engine. The outer diameter of the cross section of the second holding tube 11, crossing the central axis at right angles, is the outer diameter of a middle portion that excludes both end portions having decreased diameters. The thickness of a wall of the second holding tube 11 (the wall thickness) is preferably from 0.3 to 1.5 mm, further preferably 0.5 to 1.0 mm. If the thickness is smaller than 0.3 mm, the strength lowers. If the thickness is larger than 1.5 mm, the heat release becomes insufficient.

The end (the one end 12) of the second holding tube 11 connected to the first holding tube 1 and the opposite end thereof are formed to be thin, and a middle portion 13 of the tube is formed to be thick. Moreover, the thickness of the middle portion 13 (the diameter (the outer diameter) of the cross section of the portion crossing the central axis at right angles) is larger than that of the first holding tube 1. The thickness of the middle portion 13 of the second holding tube 11 is increased in this manner, whereby the takeout portion 23 of the particulate matter detection device 21 can easily be positioned in the second holding tube 11. When the takeout portion 23 of the particulate matter detection device 21 is connected to an external wiring line, the takeout portion 23 is brought into contact with the wiring line, pressed from the outside by the contact member 24, thus held and connected, whereby the volume of the takeout portion becomes larger than that of another portion of the particulate matter detection device 21. Therefore, the middle portion 13 of the second holding tube 11 is preferably thickened.

The end (the other end) of the second holding tube 11 which is not connected to the first holding tube 1 is opened, and the opening is preferably closed with a plug 14 made of a rubber. Moreover, the rubber plug 14 is preferably provided with a through hole through which the external wiring line to be electrically connected to the takeout portion 23 of the particulate matter detection device 21 is passed. The rubber material of the plug preferably has a high heat resistance, and examples of the material include a silicon rubber.

The first holding tube 1 is preferably firmly connected to the second holding tube 11. They are preferably connected by, for example, laser welding, Tig welding or the like. Moreover, a distance between the portion of the first holding tube 1 connected to the second holding tube 11 and the tip of the second end 3 inserted into the second holding tube 11 is preferably from 5 to 15 mm, further preferably from 6 to 8 mm. If the distance is shorter than 5 mm, the strength runs short. If the distance is longer than 15 mm, heat is confined in the tubular structure 100.

Figure 3:
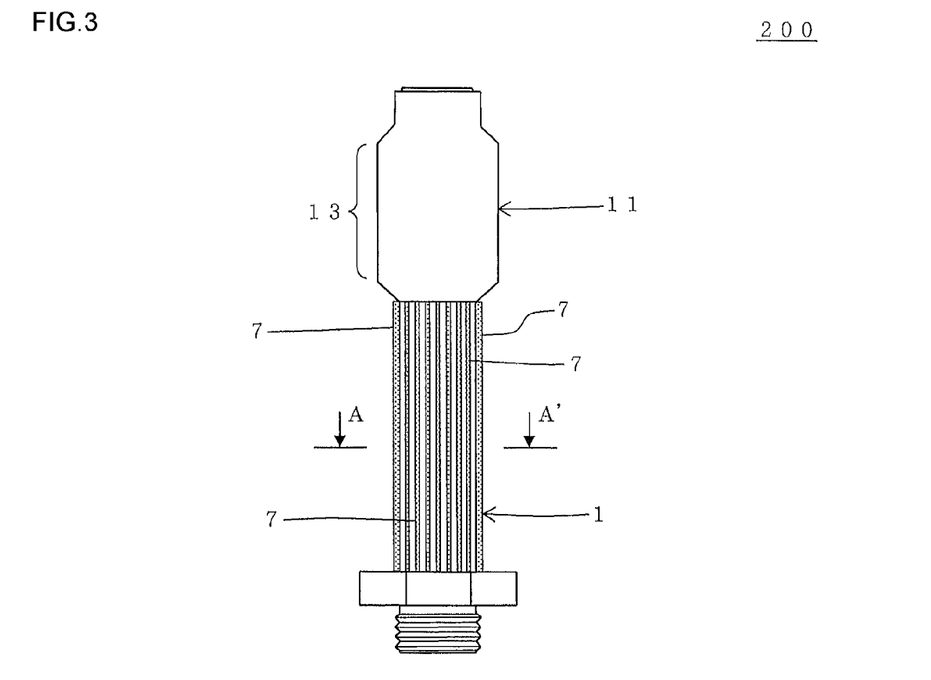
FIG. 3 is a side view schematically showing another embodiment of the tubular structure for fixing the particulate matter detection device of the present invention.
Figure 4:
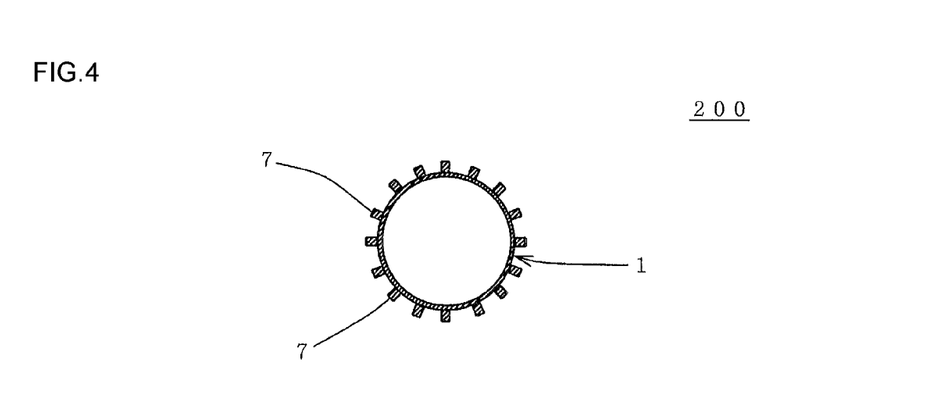
FIG. 4 is a schematic diagram showing a cross section of the tubular structure for fixing the particulate matter detection device shown in FIG. 3 cut along the A-A' line.

Next, another embodiment of the tubular structure of the present invention will be described. As shown in FIGS. 3 and 4, in a tubular structure 200 of the present embodiment, the first holding tube 1 has a plurality of linear projections 7 extending in a central axis direction over the whole outer periphery thereof. Since the first holding tube 1 has the linear projections 7, its strength can be improved. Furthermore, the surface area of the first holding tube 1 increases, and hence heat release properties can be improved. Therefore, in the tubular structure 200 of the present embodiment, since the first holding tube 1 has the linear projections 7, it is possible to obtain an effect of improving both strength and heat release properties, which cannot be obtained by a double tube. Here, "the linear projections" are raised portions linearly extending along the surface of the first holding tube. The linear projections 7 are preferably evenly disposed over the whole outer periphery of the first holding tube 1. The heights of the linear projections 7 are preferably from 0.5 to 5 mm, further preferably from 0.5 to 2 mm. If the height is smaller than 0.5 mm, the effect of improving the strength and the heat release properties decreases. If the height is larger than 5 mm, the first holding tube 1 enlarges, and cannot easily be disposed in the narrow place. Moreover, the widths of the linear projections 7 are preferably from 0.5 to 1.5 mm, further preferably from 0.5 to 1.0 mm. If the width is smaller than 0.5 mm, the strength of the linear projections 7 lowers. If the width is larger than 1.5 mm, the effect of improving the heat release properties decreases. Furthermore, the length of each linear projection 7 is preferably from 65 to 100%, further preferably from 80 to 100%, especially preferably 100% of the length of the first holding tube 1 in the central axis direction. If the length ratio is smaller than 65%, the effect of improving the strength and the heat release properties decreases. Here, the length of the first holding tube 1 in the central axis direction is not the length of the whole first holding tube but is a length between the portion of the first holding tube 1 connected to a second holding tube 11 and a flange portion 5 (the flange portion 5 is not included). That is, the length is the length of the externally exposed single tube portion of the first holding tube 1 excluding a first end 2. FIG. 3 is a side view schematically showing the other embodiment of the tubular structure for fixing the particulate matter detection device of the present invention. FIG. 4 is a schematic diagram showing a cross section of the tubular structure for fixing the particulate matter detection device shown in FIG. 3 cut along the A-A' line.

Moreover, the tubular structure 200 of the present embodiment has preferably 11 to 44 linear projections 7, further preferably 18 to 23 linear projections along the outer periphery of the first holding tube 1. If the number of the linear projections is smaller than 11, the effect of improving the strength and the heat release properties decreases. If the number is larger than 44, the effect of improving the heat release properties decreases.

In the tubular structure 200 of the present embodiment, a second holding tube 11 may also further preferably have a plurality of linear projections 7 extending in the central axis direction over the whole outer periphery thereof. Since the second holding tube 11 has the linear projections 7, its strength can be improved. Furthermore, the surface area of the second holding tube 11 increases, and hence the heat release properties can be improved. The conditions of the linear projections 7 are preferably similar to those of the linear projections 7 formed on the first holding tube 1. It is to be noted that the length of each linear projection 7 is preferably from 65 to 100%, further preferably from 80 to 100%, especially preferably 100% of the length of the middle portion 13 of the second holding tube 11 in the central axis direction. If the length ratio is smaller than 65%, the effect of improving the strength and the heat release properties decreases.

The other conditions of the tubular structure 200 of the present embodiment are preferably similar to those of the tubular structure of the above embodiment of the present invention.

Figure 5:
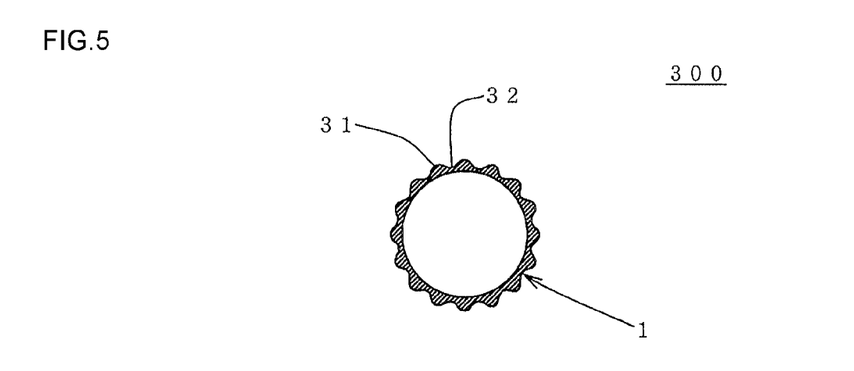
FIG. 5 is a schematic diagram showing a cross section of a portion of a first holding tube of the tubular structure of the present embodiment crossing a central axis at right angles.

Next, a still another embodiment of the tubular structure of the present invention will be described. As shown in FIG. 5, in a tubular structure 300 of the present embodiment, a first holding tube 1 preferably has a shape (a corrugated plate shape) formed by rounding a corrugated plate into a cylindrical shape, and is provided with convex portions 31 extending in a central axis direction and concave portions 32 extending in the central axis direction over the outer periphery thereof. The convex portions 31 have a ridge-like shape extending in the central axis direction. The tubular structure 300 of the present embodiment has the above corrugated plate shape, and both strength and heat release properties can be improved. FIG. 5 is a schematic diagram showing the cross section of a portion of the first holding tube 1 of the tubular structure 300 of the present embodiment crossing the central axis thereof at right angles.

The convex portions 31 are preferably evenly disposed over the whole outer periphery of the first holding tube 1. The height of each convex portion 31 (the height on the basis of the position of the adjacent concave portion 32) is preferably from 1 to 5 mm, further preferably from 1.5 to 3 mm. If the height is smaller than 1 mm, the effect of improving the strength and the heat release properties decreases. If the height is larger than 5 mm, the first holding tube 1 enlarges, and cannot be easily disposed in a narrow place. The length of the convex portion 31 is preferably from 65 to 100%, further preferably from 80 to 100%, especially preferably 100% of the length of the first holding tube 1 in the central axis direction. If the length ratio is smaller than 65%, the effect of improving the strength and the heat release properties decreases. The length of the first holding tube 1 in the central axis direction is the length of an externally exposed single tube portion of the first holding tube 1 excluding a first end 2.

Moreover, the tubular structure 300 of the present embodiment has preferably 10 to 30 convex portions 31, further preferably 14 to 22 convex portions along the outer periphery of the first holding tube 1. If the number of the convex portions is smaller than 10, the effect of improving the strength and the heat release properties decreases. If the number is larger than 30, the effect of improving the heat release properties decreases.

The other conditions of the tubular structure 300 of the present embodiment are preferably similar to those of the tubular structure of the above embodiment of the present invention.

Figure 6:
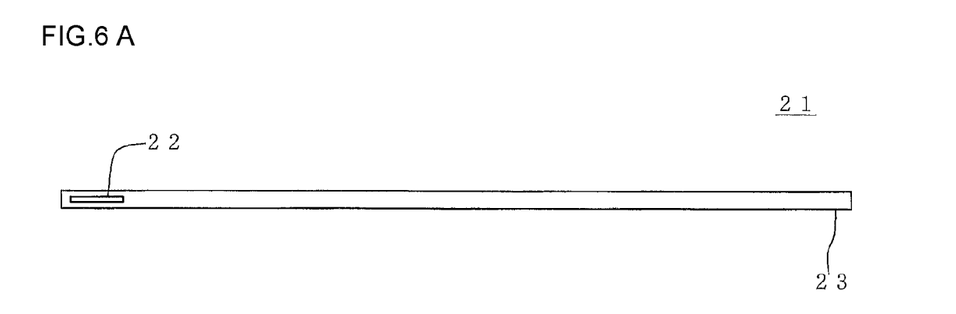
FIG. 6A is a side view showing one example of the particulate matter detection device fixed to a pipe by the tubular structure for fixing the particulate matter detection device of the present invention.
FIG. 6B is a plan view showing one example of the particulate matter detection device fixed to the pipe by the tubular structure for fixing the particulate matter detection device of the present invention.

(2) Particulate Matter Detection Device:

The particulate matter detection device fixed to the pipe through which the exhaust gas flows by the tubular structure for fixing the particulate matter detection device of the present invention is a particulate matter detection device made of a ceramic material, prolonged in one direction and having a detecting portion of a particulate matter at one end thereof and a takeout portion of a wiring line at the other end thereof. Examples of the particulate matter detection device include a particulate matter detection device described in Japanese Publication No. 2010-78428, and specifically include a plate-like particulate matter detection device 21 made of a ceramic material and shown in FIGS. 6A and 6B. In the particulate matter detection device shown in FIGS. 6A and 6B, a detecting portion 22 is constituted of a through hole, an electrode disposed therein and the like. Moreover, the particulate matter in the exhaust gas which has flowed into the through hole is electrically caused to adhere to the inner wall surface of the through hole, and the impedance or the like of the inner wall surface of the through hole is measured to detect the adhering amount of the particulate matter or the like. Moreover, at the end (the other end) of the device opposite to the detecting portion, a takeout portion 23 provided with a takeout terminal 25 is formed. The takeout terminal 25 is a portion connected to an external electric wiring line. In such a particulate matter detection device, the detecting portion 22 is directly inserted into a high-temperature pipe to measure the particulate matter, and hence the detecting portion 22 is disposed away from the takeout portion 23 so that the takeout portion 23 vulnerable to heat does not have the high temperature. Therefore, the particulate matter detection device is prolonged in one direction, and includes the detecting portion 22 disposed at one end of the device and the takeout portion 23 disposed at the other end thereof, which prevents the heat on a detecting portion 22 side from being conducted to a takeout portion 23 side. FIG. 6A is a side view showing one example of the particulate matter detection device fixed to the pipe by the tubular structure for fixing the particulate matter detection device of the present invention. FIG. 6B is a plan view showing one example of the particulate matter detection device fixed to the pipe by the tubular structure for fixing the particulate matter detection device of the present invention.

The material of the particulate matter detection device is preferably at least one selected from the group consisting of alumina, cordierite, mullite, glass, zirconia, magnesia and titania. Moreover, cordierite is further preferable, because it is excellent in resistance to thermal shock. Furthermore, the length of the particulate matter detection device is preferably from 70 to 130 mm, the thickness thereof is preferably 0.5 to 3 mm, and the width thereof (the length thereof in a direction in which a gas flows in the detecting portion) is preferably from 2 to 20 mm. Moreover, examples of the material of the takeout terminal 25 include Ni, Pt, Cr, W, Mo, Al, Au, Ag, Cu, stainless steel and Kovar.

(3) Fixing Method of Particulate Matter Detection Device:

In one embodiment of the fixing method of the particulate matter detection device of the present invention, in the above embodiment (the tubular structure 100) of the tubular structure for fixing the particulate matter detection device of the present invention, the particulate matter detection device made of the ceramic material, prolonged in one direction and having the detecting portion of the particulate matter at one end thereof and the takeout portion of the wiring line at the other end thereof is disposed so that the detecting portion projects to the outside from the first end of the first holding tube and so that the takeout portion of the wiring line is positioned in the second holding tube, and the particulate matter detection device is fixed to the pipe of the exhaust gas by the fixing structure portion of the first holding tube so that the detecting portion of the particulate matter detection device is positioned in the pipe of the exhaust gas.

In this way, according to the fixing method of the particulate matter detection device of the present embodiment, the particulate matter detection device is fixed to the pipe through which the exhaust gas flows by use of the embodiment of the tubular structure for fixing the particulate matter detection device of the present invention, whereby even when a high temperature exhaust gas circulates through the pipe, the heat release properties of the tubular structure for fixing the particulate matter detection device are satisfactory, which prevents a measured value of the device from becoming inaccurate or fluctuating.

The length of the portion of the particulate matter detection device projecting to the outside from the tip of the first end of the tubular structure is such a length that when the particulate matter detection device is attached to the tubular structure for fixing the particulate matter detection device and fixed to the pipe, the detecting portion is positioned in the center of the pipe (the center of the cross section of the pipe crossing the exhaust gas flowing direction at right angles).

Moreover, another embodiment of the fixing method of the particulate matter detection device of the present invention is a method for fixing the particulate matter detection device to the pipe by use of the other embodiment (the tubular structure 200) of the tubular structure for fixing the particulate matter detection device of the present invention, instead of the tubular structure 100, in the same manner as in the above embodiment of the fixing method of the particulate matter detection device of the present invention. In the fixing method of the particulate matter detection device of the present embodiment, since the tubular structure 200 provided with the plurality of linear projections disposed on the first holding tube is used, the fixing method is excellent in the breakdown prevention effect of the particulate matter detection device, particularly in the heat release properties as compared with the above embodiment of the fixing method of the particulate matter detection device of the present invention.

Furthermore, still another embodiment of the fixing method of the particulate matter detection device of the present invention is a method for fixing the particulate matter detection device to the pipe by use of the other embodiment (the tubular structure 300) of the tubular structure for fixing the particulate matter detection device of the present invention, instead of the tubular structure 100, in the same manner as in the above embodiment of the fixing method of the particulate matter detection device of the present invention. In the fixing method of the particulate matter detection device of the present embodiment, since the tubular structure 300 including the first holding tube having the corrugated plate-like shape is used, the fixing method is excellent in the breakdown prevention effect of the particulate matter detection device and further in the heat release properties as compared with the above embodiment of the fixing method of the particulate matter detection device of the present invention.

(4) Manufacturing Method of Tubular Structure for Fixing Particulate Matter Detection Device:

There is not any special restriction on the manufacturing method of the embodiment of the tubular structure for fixing the particulate matter detection device of the present invention, but the tubular structure for fixing the particulate matter detection device shown in, for example, FIGS. 1 and 2 can be manufactured by a method as follows.

To prepare the first holding tube, a stainless steel tube (the stainless tube) having predetermined diameter, length and thickness is prepared, and the end thereof corresponding to the first end is processed into a thread. It is to be noted that a portion corresponding to the bottom portion 6 of the particulate matter detection device fixing tubular structure 100 shown in FIGS. 1 and 2 is preferably formed by cutting the portion integrally with the tube. Moreover, the portion corresponding to the bottom portion 6 is preferably provided with a through hole through which the particulate matter detection device is passed. Then, the flange portion having a hexagonal outer shape is attached to the stainless tube by welding. Conditions such as the shape and size of the stainless tube are preferably set so as to obtain a preferable tubular structure for fixing the particulate matter detection device in the above embodiment of the present invention.

When the second holding tube is prepared, a stainless steel tube (the stainless tube) having predetermined diameter, length and thickness is prepared, and both ends are processed so as to decrease the diameters thereof. As shown in FIGS. 1 and 2, the outer shape of one end is formed into a truncated conical shape, and the outer shape of the other end is formed into a shape of a cylinder connected onto a truncated cone. Conditions such as the shape and size of the stainless tube are preferably set so as to obtain a preferable tubular structure for fixing the particulate matter detection device in the above embodiment of the present invention.

The stainless tube processed for preparing the first holding tube and the stainless tube processed for preparing the second holding tube are bonded by welding one end of the second holding tube to the end of the first holding tube which is not processed into a thread, whereby the tubular structure for fixing the particulate matter detection device as shown in FIGS. 1 and 2 is preferably obtained. As a method for welding the first holding tube to the second holding tube, laser welding, Tig welding or the like is preferable. It is to be noted that a plug may be made of a predetermined rubber.

EXAMPLES

Hereinafter, the present invention will further specifically be described with respect to examples, but the present invention is not limited to these examples.

Example 1

A tubular structure for fixing a particulate matter detection device having a shape shown in FIGS. 1 and 2 was prepared. Specifically, a stainless tube having a diameter (the outer diameter) of 14 mm, a length of 68 mm and a thickness of 0.5 mm was prepared, and the end of the tube corresponding to a first end was processed into a thread. Moreover, a portion of the tube corresponding to a bottom portion was formed by cutting the portion integrally with the tube. In the bottom portion, a rectangular through hole was formed which had a cross section of 7.1 mm×12.1 mm crossing the central axis at right angles. Moreover, a flange portion having a hexagonal outer shape was attached to a position adjacent to the position where the thread portion of the stainless tube was formed by welding, and the stainless tube processed for preparing a first holding tube was obtained.

Next, a stainless tube having a diameter (the outer diameter) of 20 mm, a length of 47 mm and a thickness of 0.5 mm was prepared. Then, both the ends of the prepared stainless tube were processed so as to decrease the diameters thereof, and as shown in FIGS. 1 and 2, the outer shape of one end was formed into a truncated conical shape, and the other end was formed into a shape of a cylinder connected onto a truncated cone, whereby the stainless tube processed for preparing a second holding tube was obtained. As to the size of the cross section of the truncated conical end cut along a plane including the central axis, an upper bottom had a size of 16.5 mm, a lower bottom had a size of 20 mm, and a height was 3 mm. Moreover, as the size of the end having a shape of the cylinder connected onto a truncated cone, in a truncated conical portion, the size of an upper bottom thereof was 14 mm, the size of a lower bottom thereof was 20 mm and a height thereof was 3 mm, and in a cylindrical portion, the diameter of the bottom surface thereof was 20 mm and a height thereof was 15 mm.

Next, the stainless tube processed for preparing the first holding tube and the stainless tube processed for preparing the second holding tube were bonded by laser-welding one end of the second holding tube to the end of the first holding tube which was not processed into a thread, whereby the tubular structure for fixing the particulate matter detection device (Example 1) was obtained as shown in FIGS. 1 and 2. The length of the first holding tube inserted into the second holding tube was 8 mm. It is to be noted that when "a strength test" and "a heat release property test" are performed as follows, particulate matter needs to adhere in the tubular structure for fixing the particulate matter detection device. Therefore, after attaching the particulate matter detection device into the stainless tube processed for preparing the first holding tube, the stainless tube for preparing the first holding tube and the stainless tube for preparing the second holding tube were bonded. Moreover, a columnar rubber plug having a bottom surface diameter of 13 mm and a height of 15 mm was prepared, and a through hole for passing a wiring line therethrough was formed. As the material of the plug, silicon rubber was used.

The obtained tubular structure for fixing the particulate matter detection device was subjected to "the strength test" and "the heat release property test" by the following methods. Results are shown in Table 1.

(Strength Test)

(1) A tubular structure for fixing particulate matter detection device (a tubular structure 100) provided with a particulate matter detection device is attached to a pseudo exhaust pipe fixed vertically to a floor surface so that the structure is parallel to the floor surface. The heater resistance value and capacitance value of the particulate matter detection device are beforehand measured. They are the "initial numeric values".

(2) A 1 m pipe is vertically disposed at a position which is 50 mm above and away from the middle portion of a tubular structure 100.

(3) A 100 g iron ball is caused to drop down into the pipe from the upper part thereof so as to strike the tubular structure 100 (the number of repetitions: 10).

(4) The heater resistance value and capacitance value of the particulate matter detection device are measured, and it is judged whether or not at least one of the heater resistance value and the capacitance value deviates from a range of ±10% of the above initial numeric values. In this stage, a case where at least one of the heater resistance value and the capacitance value deviates from the range of ±10% of the initial numeric values is "x".

(5) In a case where both of the heater resistance value and the capacitance value are in the range of ±10% of the initial numeric values, the pipe is replaced with a 2 m pipe, and the test is repeated in the same manner as in (3) (the number of the repetitions: 10).

(6) The heater resistance value and the capacitance value of the particulate matter detection device are measured and compared with the initial numeric values. A case where both of the heater resistance value and the capacitance value are in a range of ±5% of the initial numeric values is "⊚". A case where both of the heater resistance value and the capacitance value are in the range of ±10% of the initial numeric values (excluding the case where both of the heater resistance value and the capacitance value are in the range of ±5% of the initial numeric values) is "○". A case where at least one of the heater resistance value and the capacitance value deviates from the range of ±10% of the initial numeric values is "x".

(Heat Release Property Test)

(1) A thermocouple is incorporated in a contact member in the tubular structure 100 so that the temperature of the contact member can be measured.

(2) The tubular structure 100 is attached to a propane burner, and heated at a gas temperature of 900° C. for one hour.

(3) After the elapse of one hour, the temperature of the contact member which is being heated is confirmed by the thermocouple. When the temperature is 250° C.±10%, the structure is considered to pass the test. In Table 1, a case where the temperature of the contact member is 250° C.±5% is "⊚", a case where the temperature of the contact member is 250° C.±10% (250° C.±5% is not included) is "○", and a case where the temperature of the contact member deviates from the range of 250° C.±10% is "x".

The particulate matter detection device used in the strength test and the heat release property test was the same as a device usually used for measurement except for a test comparison portion.

TABLE 1

|  | Strength test | Heat release property test |
| --- | --- | --- |
| Example 1 | ○ | ○ |
| Example 2 | ⊚ | ⊚ |
| Example 3 | ⊚ | ⊚ |
| Comparative Example 1 | X | X |

Example 2

A tubular structure for fixing a particulate matter detection device (Example 2) was obtained in the same manner as in Example 1 except that linear projections were formed along the outer periphery of a first holding tube as shown in FIGS. 3 and 4. The linear projections were formed by cutting a stainless tube. Each linear projection had a height of 1 mm, a width of 1 mm, and a length of 30 mm in the central axis direction of the first holding tube, and 22 linear projections were formed with an equal space being therebetween along the outer periphery of the first holding tube. "A strength test" and "a heat release property test" were performed in the same manner as in Example 1. Results are shown in Table 1.

Example 3

A tubular structure for fixing a particulate matter detection device (Example 3) was obtained in the same manner as in Example 1 except that a first holding tube had a corrugated plate-like shape as shown in FIG. 5. The corrugated plate-like shape was formed by a press. The corrugated plate-like shape had a height of 1 mm (the height of a convex portion on the basis of an adjacent concave portion), and a length of 15 mm in the central axis direction of the first holding tube. Moreover, 22 convex portions were formed with an equal space being left therebetween along the outer periphery of the first holding tube. "A strength test" and "a heat release property test" were performed in the same manner as in Example 1. Results are shown in Table 1.

Comparative Example 1

Figure 7:
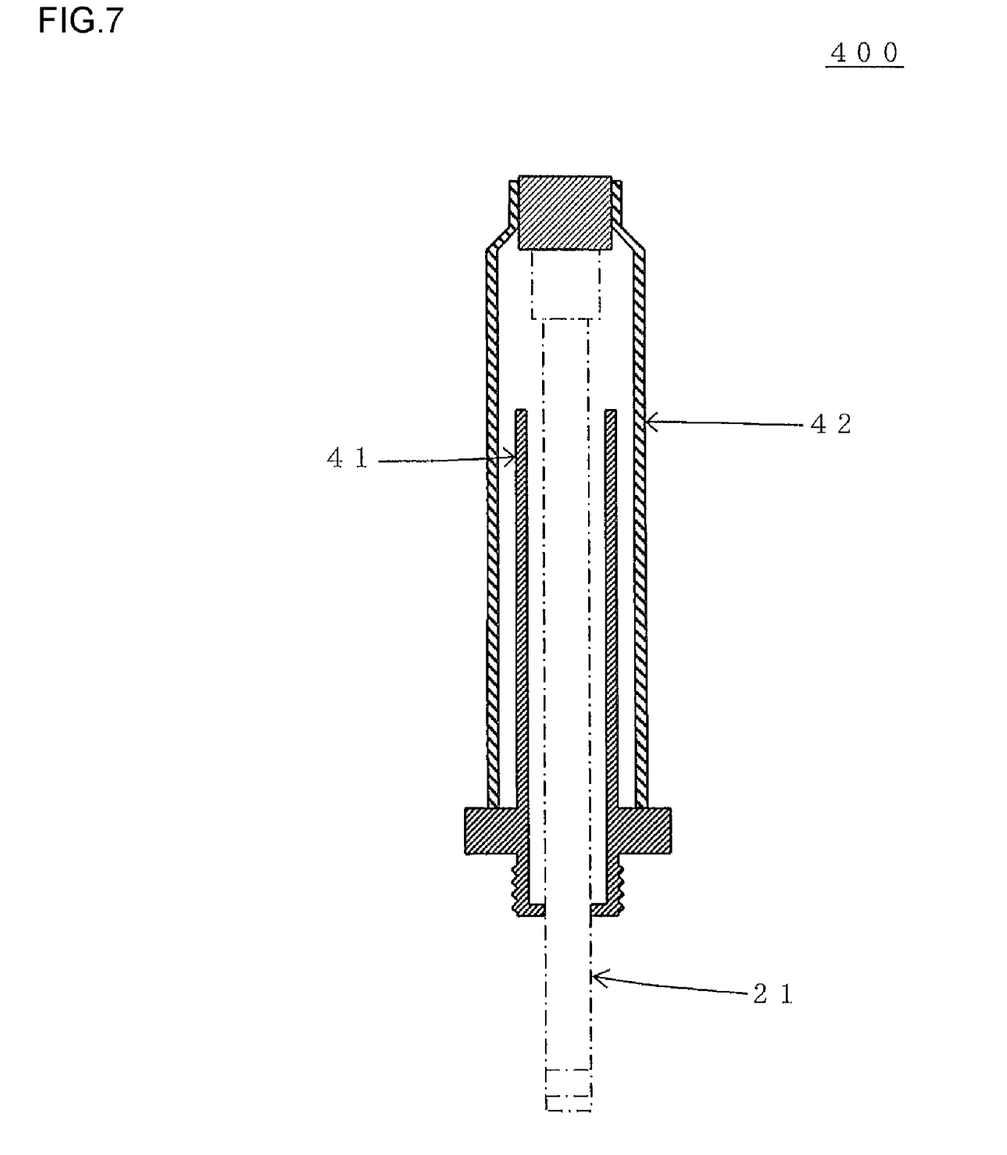
FIG. 7 is a schematic diagram showing a cross section of a tubular structure for fixing a particulate matter detection device of Comparative Example 1 cut along a plane passing along a central axis.

A tubular structure for fixing particulate matter detection device 400 (Comparative Example 1) was obtained in the same manner as in Example 1 except that a second holding tube 42 covered a first holding tube 41 from a second end thereof to a flange portion (the flange portion was not included) as shown in FIG. 7. The second holding tube was prepared by using a stainless tube having a diameter (the outer diameter) of 20 mm, a length of 70 mm and a thickness of 0.5 mm. The second holding tube was bonded to the flange portion of the first holding tube by laser welding, and the first holding tube and the second holding tube were formed so as to have a double tube structure. "A strength test" and "a heat release property test" were performed in the same manner as in Example 1. Results are shown in Table 1. FIG. 7 is a schematic diagram showing a cross section of the tubular structure for fixing particulate matter detection device of Comparative Example 1 cut along a plane passing along a central axis.

It is seen from Table 1 that the tubular structures for fixing the particulate matter detection device of Examples 1 to 3 are excellent in strength and heat release properties as compared with the tubular structure for fixing the particulate matter detection device of Comparative Example 1. Moreover, it is seen from Examples 1 and 2 that when the linear projections are formed along the outer periphery of the first holding tube, the tubular structure becomes more excellent in the strength and heat release properties. Furthermore, it is seen from Examples 1, 2 and 3 that when the first holding tube has the linear projections and the corrugated plate-like shape, the tubular structure becomes more excellent in the strength and heat release properties.

The present invention can preferably be utilized for fixing the particulate matter detection device to an exhaust pipe of a car engine or the like.

DESCRIPTION OF REFERENCE NUMERALS

1, 41: first holding tube, 2: first end, 3: second end, 4: fixing structure portion. 5: flange portion, 6: bottom portion, 7: linear projection, 11, 42: second holding tube, 12: one end, 13: middle portion, 14: plug, 21: particulate matter detection device, 22: detecting portion, 23: takeout portion, 24: contact member, 25: takeout terminal, 31: convex portion, 32: concave portion, and 100, 200, 300 and 400: tubular structure for fixing particulate matter detection device.

What is claimed is:

1. A tubular structure for fixing a particulate matter detection device, comprising:
   a tubular first holding tube having a fixing structure portion at a first end as one end thereof; and
   a tubular second holding tube having one end fixed to a second end as the other end of the first holding tube so that the second holding tube is coaxial with the first holding tube,
   wherein the particulate matter detection device made of a ceramic material, prolonged in one direction and having a detecting portion for particulate matter at one end thereof and a takeout portion of a wiring line at the other end thereof is disposed so that the detecting portion projects to the outside from the first end of the first holding tube and so that the takeout portion of the wiring line is positioned in the second holding tube, and the particulate matter detection device is fixed to a pipe of an exhaust gas by the fixing structure portion of the first holding tube so that the detecting portion of the particulate matter detection device is positioned in the pipe for the exhaust gas.

2. The tubular structure for fixing the particulate matter detection device according to claim 1, wherein the first holding tube has a plurality of linear projections extending in a central axis direction thereof over the whole outer periphery thereof.

3. The tubular structure for fixing the particulate matter detection device according to claim 2, wherein the linear projections have heights of 0.5 to 5 mm.

4. The tubular structure for fixing the particulate matter detection device according to claim 3, wherein the first holding tube has a length of 40 to 90 mm.

5. A fixing method of a particulate matter detection device, comprising the steps of: disposing, in the tubular structure for fixing the particulate matter detection device according to claim 3, the particulate matter detection device made of a ceramic material, prolonged in one direction and having the detecting portion for particulate matter at one end thereof and the takeout portion of a wiring line at the other end thereof so that the detecting portion projects to the outside from the first end of the first holding tube and so that the takeout portion of the wiring line is positioned in the second holding tube; and
   fixing the particulate matter detection device to a pipe for an exhaust gas by the fixing structure portion of the first holding tube so that the detecting portion of the particulate matter detection device is positioned in the pipe for the exhaust gas.

6. The tubular structure for fixing the particulate matter detection device according to claim 2, wherein the second holding tube has a plurality of linear projections extending in the central axis direction thereof over the whole outer periphery thereof.

7. The tubular structure for fixing the particulate matter detection device according to claim 6, wherein the linear projections have heights of 0.5 to 5 mm.

8. The tubular structure for fixing the particulate matter detection device according to claim 6, wherein the first holding tube has a length of 40 to 90 mm.

9. The tubular structure for fixing the particulate matter detection device according to claim 2, wherein the first holding tube has a length of 40 to 90 mm.

10. A fixing method of a particulate matter detection device, comprising the steps of: disposing, in the tubular structure for fixing the particulate matter detection device according to claim 2, the particulate matter detection device made of a ceramic material, prolonged in one direction and having the detecting portion for particulate matter at one end thereof and the takeout portion of a wiring line at the other end thereof so that the detecting portion projects to the outside from the first end of the first holding tube and so that the takeout portion of the wiring line is positioned in the second holding tube; and fixing the particulate matter detection device to a pipe for an exhaust gas by the fixing structure portion of the first holding tube so that the detecting portion of the particulate matter detection device is positioned in the pipe for the exhaust gas.

11. The tubular structure for fixing the particulate matter detection device according to claim 1, wherein the second holding tube has a plurality of linear projections extending in the central axis direction thereof over the whole outer periphery thereof.

12. The tubular structure for fixing the particulate matter detection device according to claim 11, wherein the linear projections have heights of 0.5 to 5 mm.

13. The tubular structure for fixing the particulate matter detection device according to claim 12, wherein the first holding tube has a length of 40 to 90 mm.

14. The tubular structure for fixing the particulate matter detection device according to claim 11, wherein the first holding tube has a length of 40 to 90 mm.

15. A fixing method of a particulate matter detection device, comprising the steps of: disposing, in the tubular structure for fixing the particulate matter detection device according to claim 11, the particulate matter detection device made of a ceramic material, prolonged in one direction and having the detecting portion for particulate matter at one end thereof and the takeout portion of a wiring line at the other end thereof so that the detecting portion projects to the outside from the first end of the first holding tube and so that the takeout portion of the wiring line is positioned in the second holding tube; and fixing the particulate matter detection device to a pipe for an exhaust gas by the fixing structure portion of
the first holding tube so that the detecting portion of the particulate matter detection device is positioned in the pipe for the exhaust gas.

16. The tubular structure for fixing the particulate matter detection device according to claim 1, wherein the first holding tube has a length of 40 to 90 mm.

17. A fixing method of a particulate matter detection device, comprising the steps of: disposing, in the tubular structure for fixing the particulate matter detection device according to claim 16, the particulate matter detection device made of a ceramic material, prolonged in one direction and having the detecting portion for particulate matter at one end thereof and the takeout portion of a wiring line at the other end thereof so that the detecting portion projects to the outside from the first end of the first holding tube and so that the takeout portion of the wiring line is positioned in the second holding tube; and fixing the particulate matter detection device to a pipe for an exhaust gas by the fixing structure portion of the first holding tube so that the detecting portion of the particulate matter detection device is positioned in the pipe for the exhaust gas.

18. The tubular structure for fixing the particulate matter detection device according to claim 1, wherein the fixing structure portion of the first holding tube has a thread structure.

19. A fixing method of a particulate matter detection device, comprising the steps of: disposing, in the tubular structure for fixing the particulate matter detection device according to claim 18, the particulate matter detection device made of a ceramic material, prolonged in one direction and having the detecting portion for particulate matter at one end thereof and the takeout portion of a wiring line at the other end thereof so that the detecting portion projects to the outside from the first end of the first holding tube and so that the takeout portion of the wiring line is positioned in the second holding tube; and fixing the particulate matter detection device to a pipe for an exhaust gas by the fixing structure portion of the first holding tube so that the detecting portion of the particulate matter detection device is positioned in the pipe for the exhaust gas.

20. A fixing method of a particulate matter detection device, comprising the steps of: disposing, in the tubular structure for fixing the particulate matter detection device according to claim 1, the particulate matter detection device made of a ceramic material, prolonged in one direction and having the detecting portion for particulate matter at one end thereof and the takeout portion of a wiring line at the other end thereof so that the detecting portion projects to the outside from the first end of the first holding tube and so that the takeout portion of the wiring line is positioned in the second holding tube; and fixing the particulate matter detection device to a pipe for an exhaust gas by the fixing structure portion of the first holding tube so that the detecting portion of the particulate matter detection device is positioned in the pipe for the exhaust gas.

* * * * *